(12) United States Patent
Shirotake et al.

(10) Patent No.: US 10,351,644 B2
(45) Date of Patent: Jul. 16, 2019

(54) ANTIVIRAL DRUG

(71) Applicant: Shoichi Shirotake, Yokohama-shi, Kanagawa (JP)

(72) Inventors: Shoichi Shirotake, Yokohama (JP); Syun-ichirou Oshima, Nankoku (JP); Masayuki Imajoh, Nankoku (JP)

(73) Assignee: Shoichi Shirotake, Yokohama-Shi (JP)

(*) Notice: Subject to any disclaimer, the term of this patent is extended or adjusted under 35 U.S.C. 154(b) by 95 days.

(21) Appl. No.: 15/122,074

(22) PCT Filed: Feb. 26, 2015

(86) PCT No.: PCT/JP2015/055552
§ 371 (c)(1),
(2) Date: Dec. 1, 2016

(87) PCT Pub. No.: WO2015/129793
PCT Pub. Date: Sep. 3, 2015

(65) Prior Publication Data
US 2017/0073442 A1    Mar. 16, 2017

(30) Foreign Application Priority Data
Feb. 27, 2014  (JP) ................................ 2014-036710

(51) Int. Cl.
| A01N 37/34 | (2006.01) |
| A61K 31/785 | (2006.01) |
| C08F 122/32 | (2006.01) |
| A61K 47/36 | (2006.01) |
| A61K 31/78 | (2006.01) |
| A61K 9/16 | (2006.01) |
| A61K 47/18 | (2017.01) |
| A61K 47/20 | (2006.01) |
| A61K 47/22 | (2006.01) |
| A61K 47/24 | (2006.01) |
| A61K 47/26 | (2006.01) |

(52) U.S. Cl.
CPC ............ *C08F 122/32* (2013.01); *A01N 37/34* (2013.01); *A61K 9/1635* (2013.01); *A61K 31/78* (2013.01); *A61K 31/785* (2013.01); *A61K 47/36* (2013.01); *A61K 47/18* (2013.01); *A61K 47/20* (2013.01); *A61K 47/22* (2013.01); *A61K 47/24* (2013.01); *A61K 47/26* (2013.01)

(58) Field of Classification Search
CPC ..... C08F 122/32; A01N 37/34; A61K 9/1635; A61K 31/785; A61K 47/36; A61K 47/18; A61K 47/20; A61K 47/22; A61K 47/24; A61K 47/26
See application file for complete search history.

(56) References Cited

U.S. PATENT DOCUMENTS

| 6,881,421 B1 | 4/2005 | da Silveira et al. |
| 2010/0285140 A1 | 11/2010 | Shirotake |
| 2012/0027821 A1* | 2/2012 | Shirotake et al. |
| 2014/0065222 A1 | 3/2014 | Shirotake |
| 2015/0004202 A1 | 1/2015 | Shirotake |

FOREIGN PATENT DOCUMENTS

| EP | 2 236 143 A1 | 10/2010 |
| EP | 2 404 598 A1 | 1/2012 |
| EP | 2 692 742 A1 | 2/2014 |
| JP | 2008-127538 A | 6/2008 |
| WO | WO 96/31231 A1 | 10/1996 |
| WO | WO 2008/126846 A1 | 10/2008 |

OTHER PUBLICATIONS

Wu et al. (Macromol. Symp. 2009, 281, 39-46).*
Zhang et al. (PLoS Biology, vol. 4, Issue 1, Published Jan. 2006, pp. 0108-0118).*
Vauthier et al., "Poly(alkylcyanoacrylates) as biodegradable materials for biomedical applications," Advanced Drug Delivery Reviews (2003), vol. 55, pp. 519-548.
Song et al., "Synthesis and Antiviral Activity of Novel Chiral Cyanoacrylate Derivatives," J. Agric. Food Chem. (2005), vol. 53, pp. 7886-7891.

* cited by examiner

*Primary Examiner* — Alma Pipic
(74) *Attorney, Agent, or Firm* — Birch, Stewart, Kolasch & Birch, LLP

(57) ABSTRACT

Novel antiviral means is disclosed. The antiviral agent of the present invention comprises as an effective ingredient particles having a particle diameter of not more than 5 μm, wherein said particles are polymer particles whose repeat unit comprises a structure represented by a particular general formula, and wherein said particles do not contain an antiviral active component. The polymer particles are preferably cyanoacrylate polymer particles. The antiviral agent of the present invention shows adhesiveness to the surface (especially envelope) of virus particles, and destroys a normal virus particle structure to reduce or eliminate infectivity of the virus particles. Sanitary articles such as masks comprising the antiviral agent of the present invention can exert an excellent effect on prevention of infection with viruses such as influenza virus that occurs through droplet infection or airborne infection.

19 Claims, 3 Drawing Sheets
Specification includes a Sequence Listing.

SEQUENCE LISTING

```
<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Real-time PCR probe

<400> SEQUENCE: 1
cttcctctgc tcggcgagca cg                                              22

<210> SEQ ID NO 2
<211> LENGTH: 18
<212> TYPE: DNA
<213> ORGANISM: Artificial Sequence
<220> FEATURE:
<223> OTHER INFORMATION: Primer KHV-86F

<400> SEQUENCE: 2
gacgccggag accttgtg                                                   18

<210> SEQ ID NO 3
<211> LENGTH: 24
<212> TYPE: DNA
<213> ORGANISM: Artificial Sequence
<220> FEATURE:
<223> OTHER INFORMATION: Primer KHV-163R

<400> SEQUENCE: 3
cgggttctta tttttgtcct tgtt                                            24
```

ANTIVIRAL DRUG

TECHNICAL FIELD

The present invention relates to an antiviral agent comprising as an effective ingredient particles constituted by a polymer such as a cyanoacrylate polymer.

BACKGROUND ART

Mainly aiming at application to pharmaceuticals for human, in order to improve the effect of pharmaceuticals by drug delivery system (DDS) or by sustained release, studies of nano-encapsulation of drugs are now under way. For example, DDS in which a drug is encapsulated in cyanoacrylate polymer particles is known (Patent Documents 1, 2 and Non-patent Document 1). The present inventor and co-workers also have disclosed a method for producing cyanoacrylate polymer particles with little irregularity in particle diameter, antibiotic-containing particles, and plasmid-containing particles (Patent Documents 3 to 5). In a conventional method for synthesizing polymer particles, a saccharide(s) and/or a polysorbate(s) is(are) made to be present in the polymerization reaction system. These past studies aimed at DDS or sustained release of drugs.

The present inventors then discovered that cyanoacrylate polymer particles per se have an antibacterial activity against Gram-positive bacteria (Patent Document 6). The present inventors also discovered that amino acid-containing cyanoacrylate polymer particles have an anticancer activity and can exert antibacterial activity against various bacteria irrespective of their Gram staining properties (Patent Documents 7 to 9). Nano-sized polymer particles specifically adhere to the surface of bacteria to cause their bacteriolysis. Cyanoacrylate nanoparticles exert antibacterial activity by an action mechanism that is completely different from those of antibiotics, and are therefore effective for multidrug-resistant bacteria such as MRSA and VRE.

On the other hand, effects of nano-sized polymer particles against viruses are not known.

PRIOR ART DOCUMENTS

Patent Documents

Patent Document 1: JP H11-503148 A
Patent Document 2: JP 2002-504526 A
Patent Document 3: JP 2008-127538 A
Patent Document 4: WO 2008/126846
Patent Document 5: JP 2008-208070 A
Patent Document 6: WO 2009/084494
Patent Document 7: WO 2010/101178
Patent Document 8: WO 2012/133648
Patent Document 9: WO 2013/108871

Non-Patent Document

Non-patent Document 1: Christine Vauthier et al., Adv. Drug Deliv. Rev., 55, 519-548 (2003)

SUMMARY OF THE INVENTION

Problems to be Solved by the Invention

An object of the present invention is to provide novel antiviral means.

Means for Solving the Problems

As a result of intensive study, the present inventors discovered that polymer particles having a particular chemical structure can adhere to the surface of virus particles to destroy a normal virus particle structure, and hence can exert an antiviral action, thereby completing the present invention.

That is, the present invention provides an antiviral agent comprising as an effective ingredient particles having a particle diameter of not more than 5 µm, wherein said particles are polymer particles whose repeat unit comprises a structure represented by the following General Formula (I):

$$\left[\begin{array}{c} Z \\ | \\ -C- \\ | \\ C=O \\ | \end{array}\right] \quad (I)$$

[wherein Z represents an electron-withdrawing group], and wherein said particles do not contain an antiviral active component. The present invention also provides a method for reducing or eliminating infectivity of a virus(es), or for suppressing replication of a virus(es), which method comprises bringing an effective amount of the above-described particles into contact with the virus(es) to be suppressed. The present invention further provides a method for treating or preventing virus infection, which method comprises administering an effective amount of the above-described particles to a subject in need thereof. The present invention further provides a method for controlling a plant virus disease(s), which method comprises bringing an effective amount of the particles into contact with a plant body, plant seed, ground soil, pot soil, seedling box, agricultural equipment, or gardening tool. The present invention further provides a sanitary article material comprising the antiviral agent of the present invention. The present invention further provides a sanitary article comprising the antiviral agent of the present invention.

Effect of the Invention

By the present invention, a novel antiviral agent with which a virus(es) can be controlled using particles of a polymer such as a cyanoacrylate polymer was provided. As for known antiviral agents, a therapeutic agent targeting a transcription factor or a life cycle that is unique to each virus often has to be used for each virus. In contrast, the antiviral agent of the present invention destroys the normal structure of virus particles by its adhesiveness to the surface (especially envelope) of virus particles, thereby eliminating infectivity of the virus particles. Thus, the antiviral agent of the present invention can widely exhibit antiviral activity not only against animal viruses infectious to animals such as mammals, birds and fishes, but also against a variety of viruses including plant viruses. Sanitary articles such as masks containing the antiviral agent of the present invention can exert an excellent effect on prevention of virus infection that occurs through droplet infection or airborne infection, such as infection with influenza virus.

BRIEF DESCRIPTION OF THE DRAWINGS

FIG. 1 shows results obtained by adding a cyprinid herpes virus CyHV-3 treated with dextran-containing nanoparticles to carp fin cultured cells, incubating the cells for a predetermined period, and then determining the copy number of a viral gene (ORF89 gene) in the cells.

FIG. 2 shows results obtained by adding CyHV-3 treated with glycine-containing nanoparticles to carp fin cultured cells, incubating the cells for a predetermined period, and then determining the copy number of the ORF89 gene in the cells.

MODE FOR CARRYING OUT THE INVENTION

Figure 3:
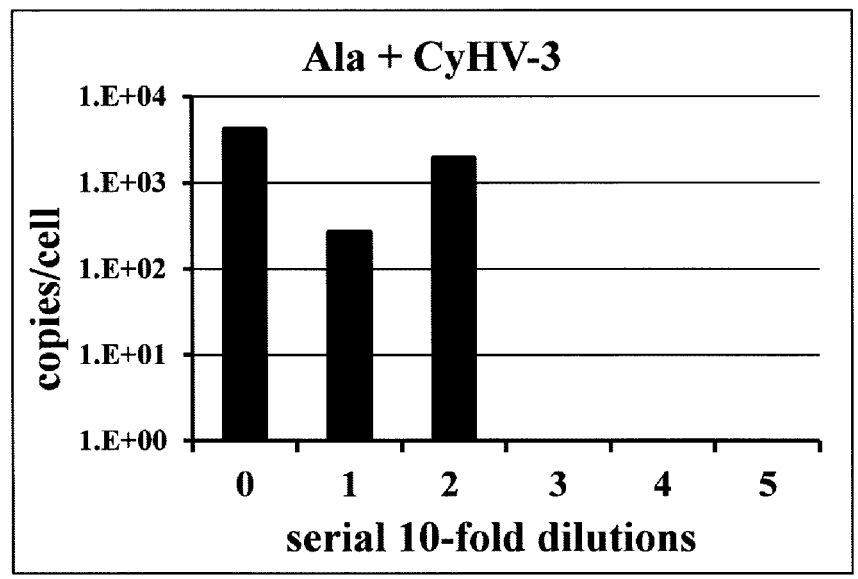
FIG. 3 shows results obtained by adding CyHV-3 treated with alanine-containing nanoparticles to carp fin cultured cells, incubating the cells for a predetermined period, and then determining the copy number of the ORF89 gene in the cells.

The antiviral agent of the present invention comprises as an effective ingredient polymer particles with a particle diameter of not more than 5 μm whose repeat unit comprises a structure represented by the following General Formula (I):

$$\begin{array}{c} Z \\ | \\ -C- \\ | \\ C=O \\ | \\ \sim \end{array} \quad (I)$$

[wherein Z represents an electron-withdrawing group]. Each wavy line in the formula represents another structure in the polymer structure, to which the structure represented by General Formula (I) is bound. The structure of General Formula (I), which has an electron-withdrawing group and a carboxyl group present at α-position, shows high affinity to glycoproteins. On the other hand, on the surface of a virus particle, especially on the envelope, viral glycoproteins are present. It is therefore thought that polymer particles having the structure of General Formula (I) show high affinity to the surface of virus particles, and specifically adhere to the surface of the virus particles, causing destruction of the envelope, leading to reduction or elimination of infectivity of the virus particles.

Specific examples of the Z group include cyano, nitro, carbonyl, carboxy, and trifluoromethyl. The Z group is preferably cyano.

Examples of the structure represented by General Formula (I) include, but are not limited to, the structure represented by the following General Formula (II).

$$\begin{array}{c} Z \\ | \\ -C- \\ | \\ C=O \\ | \\ R \end{array} \quad (II)$$

[wherein Z has the same definition as in the General Formula (I); R represents hydrogen, hydroxy, $C_1$-$C_{10}$ alkyl, $C_1$-$C_{10}$ alkoxy, $C_6$-$C_{15}$ aryl, $C_6$-$C_{15}$ aryloxy, $C_7$-$C_{16}$ aralkyl, or $C_7$-$C_{16}$ aralkyloxy; and one or more carbon atoms constituting the carbon chain in R are optionally replaced by nitrogen, sulfur, and/or oxygen].

Among the General Formula (II), a structure in which R represents hydroxy or $C_1$-$C_{10}$ alkoxy is preferred, and a structure in which R represents n-butoxy is especially preferred. Preferred examples of Z are as described above. Thus, as the structure represented by the General Formula (II), a structure in which Z represents cyano and R represents n-butoxy is especially preferred.

The polymer particles whose repeat unit comprises a structure represented by the above-described General Formula (II) can be produced by, for example, polymerizing at least one kind of monomers represented by the following General Formula (III):

$$\begin{array}{c} Z \\ | \\ X-C-Y \\ | \\ C=O \\ | \\ R \end{array} \quad (III)$$

[wherein Z and R have the same meanings as in the General Formula (II) above; and X and Y each independently represent an atomic group having a terminal carbon-carbon double bond, or X and Y together represent methylidene] in the presence of at least one selected from the group consisting of amino acids, amino acid derivatives, oligomers and polymers thereof, saccharides, and polysorbates. Examples of the monomer having such a structure include acrylate monomers. Various acrylate monomers are commercially available, and such commercially available products may be preferably used. Other monomers can be easily prepared from, for example, commercially available acrylate monomers, by well-known conventional methods in the field of chemical synthesis.

The monomer represented by General Formula (III) is preferably a monomer in which R represents hydroxy or $C_1$-$C_{10}$ alkoxy, that is, an acrylate monomer substituted by the electron-withdrawing group Z. The Z group is especially preferably cyano. That is, the monomer is especially preferably a cyanoacrylate monomer. Preferred examples of the cyanoacrylate monomer include methyl-2-cyanoacrylate, ethyl-2-cyanoacrylate, n-propyl-2-cyanoacrylate, i-propyl-2-cyanoacrylate, n-butyl-2-cyanoacrylate, i-butyl-2-cyanoacrylate, n-pentyl-2-cyanoacrylate, n-hexyl-2-cyanoacrylate, n-heptyl-2-cyanoacrylate, and n-octyl-2-cyanoacrylate. Among these, n-butyl-2-cyanoacrylate (nBCA) represented by the following formula, which has been used as an adhesive for wound closure in the field of surgery, can be especially preferably used.

$$H_2C=\overset{CN}{\underset{COO(nC_4H_9)}{C}}$$

Monomer molecules having the above-described structure can be polymerized by anionic polymerization. In the anionic polymerization, for the purpose of initiation and stabilization of the polymerization, saccharides and polysorbates, as well as amino acids, amino acid derivatives, and oligomers and polymers thereof (hereinafter collectively referred to as "amino acid-based molecule") may be used. These polymerization initiators/stabilizers may be used individually, or two or more of them may be used in combination. That is, the polymer particles used in the present invention may be particles containing at least one selected from the group consisting of amino acids, amino acid derivatives, oligomers and polymers thereof, saccharides, and polysorbates. A polymerization initiator/stabilizer that is preferably used may be, but is not limited to, at least one selected from the group consisting of amino acids, amino acid derivatives, oligomers thereof, and saccharides, or at least one selected from the group consisting of amino acids and saccharides.

Methods for producing polymer particles using a saccharide(s) and/or a polysorbate(s) as a polymerization initiator/stabilizer are known, and described in, for example, Patent Document 3, Patent Document 4 (antibiotic-containing particles), and Patent Document 5 (plasmid-containing particles). Methods for producing polymer particles using an amino acid-based molecule(s) as a polymerization initiator/stabilizer are known, and described in, for example, Patent Documents 8 and 9 (use of an amino acid-based molecule(s) alone). Patent Document 7 describes a production method using a combination of an amino acid(s) and a saccharide(s)/polysorbate(s).

In the present invention, the term "amino acid" refers to a compound which has an amino group(s) and a carboxy group(s) in the molecule, and as generally defined, the term also includes imino acids, which are cyclic secondary amine compounds in which a hydrogen of an amino group is substituted with another moiety in the molecule. Representative examples of the amino acid which may be used in the present invention include the 20 kinds of α-amino acids which constitute natural proteins, but the examples are not restricted thereto and also include β-, γ- and δ-amino acid-based molecules and the like. Specific examples thereof include, but not limited to, arginine, histidine, lysine, aspartic acid, glutamic acid, alanine, glycine, leucine, valine, isoleucine, serine, threonine, phenylalanine, tryptophan, tyrosine, cystine or cysteine, glutamine, asparagine, proline, methionine, β-alanine, γ-aminobutyric acid (GABA; neurotransmitter), carnitine, γ-aminolevulinic acid, γ-aminovaleric acid and the like.

The term "amino acid derivative" refers to a compound having a structure in which any of the groups in the amino acid as defined above is(are) modified or substituted. Amino acid derivatives which naturally occur as biogenic substances may be usually preferably used in the present invention. Specific examples of the amino acid derivative which may be used include, but are not limited to, creatine (an arginine derivative, 1-methylguanidinoacetic acid), ornithine (an arginine derivative, product of urea cycle), thyroxine (triiodothyronine; T4, belonging to aromatic amino acids), desmosine (a component of corneum elastin and collagen; having a structure in which side chains of three allysine molecules and a side chain of one lysine molecule are bound), hydroxyproline and hydroxylysine (components of gelatin and collagen), phosphoserine (an ester of serine and phosphoric acid; a component of casein), theanine (a tee component, glutamic acid derivative), kainic acid (an anthelmintic component of Corsican weed), tricholomic acid (a component of Lyophyllum), sarcosine (a component of yolks, ham, legumes; N-methylglycine) and the like.

The term amino acid "oligomer" refers to an oligopeptide in which not more than 10 amino acid residues are bound by a peptide bond(s), and the term amino acid "polymer" refers to a polypeptide in which not less than 11 amino acid residues are bound by peptide bonds. Both may comprise not only an amino acid(s) but also an amino acid derivative(s) as residues. The upper limit of the number of the residues of polypeptide is not restricted, and for example, may be not more than 500 residues. A polypeptide of 11-100 residues, 11-50 residues, 11-30 residues, 11-20 residues, or 11-15 residues may be preferably used.

Oligopeptides may be more preferably used than polypeptides. In particular, oligopeptides having 2 to 7 residues, 2 to 5 residues, or 2 or 3 residues may be more preferably used.

As described in Patent Documents 8 and 9, any of the 20 kinds of α-amino acids constituting naturally occurring proteins (that is, arginine, histidine, lysine, aspartic acid, glutamic acid, alanine, glycine, leucine, valine, isoleucine, serine, threonine, phenylalanine, tryptophan, tyrosine, cystine or cysteine, glutamine, asparagine, proline, and methionine) can be used for synthesizing nano-sized (less than 1000 nm) cyanoacrylate polymer particles under conditions where neither a saccharide nor a polysorbate is used. It has been shown that any of neutral, acidic, and basic amino acids, or any of linear, aromatic, imino, and sulfur-containing structures, can be used for producing nano-sized polymer particles having a uniform particle diameter, using neither a saccharide nor a polysorbate. Thus, not only the 20 kinds of α-amino acids, but also the above-described other amino acids and amino acid derivatives, can be used for the synthesis of nanoparticles. Oligopeptides and polypeptides can also be used for the synthesis of polymer particles since they have amino acid structures in the molecules.

The "saccharide" includes monosaccharides having a hydroxyl group(s) (e.g., glucose, mannose, ribose, and fructose), disaccharides having a hydroxyl group(s) (e.g., maltose, trehalose, lactose, and sucrose), and polysaccharides having a hydroxyl group(s) (e.g., dextran and mannan). These saccharides may be either in a cyclic form or in a linear form. The cyclic form may be either a pyranose form or a furanose form. There are various isomers of saccharides, and any of such isomers may be used. Among the saccharides described above, glucose and dextran are advantageous in view of the cost since they can be inexpensively obtained. As for dextran, dextran having an average molecular weight of about 50,000 or more is preferred. The upper limit of the molecular weight of dextran is not restricted, and the molecular weight is usually about 500,000 or less.

The "polysorbate" includes Tween surfactants such as polyoxyethylene sorbitan monolaurate (trade name, Tween 20) and polyoxyethylene sorbitan monooleate (trade name, Tween 80). Among these, Tween 20 (trade name) is advantageous in view of the cost since it can be inexpensively obtained.

In the anionic polymerization step, at least one of the above-described polymerization initiators/stabilizers may be dissolved in an appropriate solvent, and at least one kind of monomers may then be added to the resulting solution with stirring, followed by allowing the polymerization reaction to proceed while continuing stirring as appropriate. Only one kind of monomers may be used, or two or more kinds of monomers may be used.

In cases where a saccharide and/or a polysorbate is/are used as the polymerization initiator/stabilizer, the concentration of the saccharide and/or the polysorbate (if a plurality of kinds of saccharides and/or polysorbates are used, their total concentration) in the polymerization reaction solution at the beginning of the reaction is usually, but not limited to, about 0.5% to 10%, preferably about 0.75% to 7.5%. As used herein, the concentration of saccharides means w/v %, and the concentration of polysorbates means v/v %. For example, in the case where only a saccharide(s) is/are used, the above-described concentration ranges mean "0.5 w/v % to 10 w/v %" and "0.75 w/v % to 7.5 w/v %", respectively. In the case where 5 w/v % saccharide and 1 v/v % polysorbate are used in combination, their total concentration is expressed as 6%. It should be noted that, in the case where a monosaccharide(s) (e.g. glucose) is(are) used alone, the monosaccharide(s) is(are) preferably used at a concentration of about 2.5 w/v % to 10 w/v %.

In the case where an amino acid-based molecule(s) is/are used as the polymerization initiator/stabilizer, the concentration of the amino acid-based molecule (if a plurality of kinds of amino acid-based molecules are used, their total concentration) in the polymerization reaction solution at the beginning of the reaction is usually, but not limited to, about 0.1 w/v % to 3 w/v %. In the case where the amino acid-based molecule(s) is/are used in combination with a saccharide(s) and/or a polysorbate(s), the concentration of the amino acid-based molecule(s) used may be lower than the above-described concentration.

As the solvent for the polymerization reaction, an aqueous solvent composed mainly of water (e.g., water, aqueous solution of lower alcohol, or the like) may be used. Usually, water is preferably used. Since the anionic polymerization is initiated by hydroxide ions, the polymerization rate is influenced by pH of the reaction solution. When pH of the reaction solution is high, polymerization proceeds rapidly because of a high concentration of hydroxide ion. When pH is low, polymerization proceeds slowly. An appropriate polymerization rate is usually obtained under acidic conditions at a pH of about 2 to 4. In the case where an amino acid-based molecule(s) is/are used as the polymerization initiator/stabilizer, an appropriate polymerization rate is usually attained under an acidic condition of about pH 1.5 to 3.0. The acid added to the reaction solution in order to acidify it is not restricted, and not only inorganic acids but also organic acids can be used. For example, hydrochloric acid may be preferably used for the production of the polymer particles, since it does not adversely affect the reaction and evaporates after the reaction. However, the acid that may be used is not limited to hydrochloric acid. The concentration of hydrochloric acid is not limited, and may be appropriately selected within the range of about 0.0005 N to 0.5 N.

The monomer concentration in the polymerization reaction solution (if two or more kinds of monomers are used, their total concentration) at the beginning of the reaction is not limited, and usually about 0.5 v/v % to 2.0 v/v %, preferably about 0.8 v/v % to 1.2 v/v %.

The reaction temperature is not limited. The reaction is preferably simply carried out at room temperature. Since the reaction rate varies depending on the pH of the reaction solution, the type of the solvent, and the like, the reaction time is appropriately selected depending on such factors. The reaction time is not limited, and usually about 10 minutes to 5 hours, preferably about 30 minutes to 4 hours. The polymer particles obtained are usually used as neutral particles. Thus, after the reaction, a base such as an aqueous sodium hydroxide solution or the like is preferably added to the reaction solution to perform neutralization. The reaction solution after the reaction may be filtered through a filter, and the particles may be washed with sterile water as appropriate and then collected.

In terms of the size of the polymer particles used in the present invention, the average particle diameter is preferably less than 1000 nm. According to the above-described method, nano-sized polymer particles having an average particle diameter of less than 1000 nm can be easily produced. The particles produced can be collected by a conventional method such as centrifugal ultrafiltration. The lower limit of the particle diameter is not restricted. The particle diameter of the particles produced by the above-described polymerization reaction is usually not less than about 7 nm. The average particle diameter of the particles is preferably 20 nm to 600 nm, more preferably 50 nm to 550 nm. The size of the particles can be controlled by changing the acrylate monomer concentration in the reaction solution, the pH, and/or the reaction time. In the case where at least one selected from saccharides and polysorbates is used as the polymerization initiator/stabilizer, the particle size can also be controlled by changing the concentration and the kind of the polymerization initiator/stabilizer (see Patent Documents 3 and 4). In general, in cases where the pH of the reaction solution is high, where the reaction time is long, and/or where the saccharide concentration in the reaction solution is low, the particle diameter becomes large, and, in cases where a polysorbate is used as the polymerization initiator/stabilizer, the particle diameter becomes small. By appropriately combining these reaction conditions, particles having a desired size can be produced.

The charge (zeta potential) of the polymer particles is not limited, and usually about −50 mV to 0 mV. The zeta potential indicates the charge on the particle surface, and can be used as an indicator of dispersibility of the particles. The particle size and the zeta potential can be easily measured using, for example, a commercially available device utilizing He—Ne laser (e.g., Zetasizer manufactured by Malvern Inst., UK).

It is thought that, in polymer particles produced using an amino acid-based molecule as the polymerization initiator/stabilizer, the amino acid-based molecule is contained not only by simple adhesion to the particles, but also by covalent bonding of the —COO group in the amino acid structure to the carbon at the ethylene terminus of the acrylate. By using a functional group in the amino acid-based molecule covalently bound to the polymer portion, the polymer particles can be immobilized on a desired material by covalent bonding.

The content of the amino acid-based molecule in the particles obtained by the above-described method is usually about 20% to about 65%. For calculation of the content of the amino acid-based molecule, the absorbance of the filtrate obtained by filter washing after the polymerization is measured at an appropriate wavelength. The amount of the amino acid-based molecule in the filtrate (that is, the amount of the amino acid-based molecule unbound to the particles) is determined by the absorbance method. Thereafter, the content of the amino acid-based molecule can be calculated according to the following equations.

Amount of amino acid-based molecule contained=(Amount of amino acid-based molecule added)−(Amount of amino acid-based molecule in filtrate)

Content of amino acid-based molecule (%)=Amount of amino acid-based molecule contained÷Amount of amino acid-based molecule added×100

The antiviral agent of the present invention is preferably used against viruses having an envelope. Specific examples of the virus having an envelope include, but are not limited to, influenza virus, various herpes viruses (herpes simplex virus, varicella-zoster virus, cytomegalo virus, cyprinid herpes virus, and the like), human immunodeficiency virus, and Sendai virus. Among plant viruses, examples of the virus having an envelope include viruses whose intermediate host is an animal such as an insect. Specific examples of the plant virus having an envelope include, but are not limited to, viruses belonging to the family Rhabdoviridae, such as lettuce necrotic yellows virus and potato yellow dwarf virus; and viruses belonging to the genus *Tospovirus*, such as tomato spotted wilt virus.

In the present invention, the term "animal viruses" means viruses whose hosts of infection are animals such as mammals, birds, fishes, crustaceans, shellfishes/mollusks, reptiles, amphibians, and insects. The term "plant viruses" includes not only viruses whose hosts of infection are limited to plants, but also viruses whose infection to plants occurs through animal intermediate hosts such as insects.

In the present invention, the meaning of the term "antiviral" includes prevention of infection with viruses, suppression of replication of viruses, and treatment and prevention of viral infectious diseases. In cases where the term is used for plants, its meaning also includes control of plant viral diseases.

As described above, the polymer particles used in the present invention have a structure having high affinity to viral glycoprotein present on the surface, especially on the envelope, of virus particles. By electron microscopic observation of virus particles brought into contact with polymer particles, it has been found that the polymer particles adhere to the envelope to destroy the envelope. Viruses having an envelope lose their infectivity when the envelope is lost. Thus, the antiviral agent of the present invention can be preferably used as a viral infection-preventing agent. The antiviral agent of the present invention is also useful as a therapeutic or prophylactic agent for virus infections that is used by administration to a living body such as an animal, fish or the like, since the antiviral agent of the present invention is thought to be capable of reducing or eliminating infectivity of virus particles with an envelope to inhibit further infection of other cells in the living body, thereby suppressing the replication of the virus in the living body. It is known that polymer particles produced by the above-described anionic polymerization do not damage normal mammalian cells, and that, even oral administration of the polymer particles at 50 mg/body or parenteral administration of the polymer particles at 10 mg/body does not cause abnormalities nor in vivo toxicity in mice (see Patent Documents 8 and 9).

The polymer particles used in the present invention do not contain an antiviral active component against the target virus. The "antiviral active component" means a chemical substance which inhibits the function of a gene specific to a virus or its transcript, or a substance which acts on the antiviral immune mechanism of the host organism against a target virus, to inhibit the replication of the virus in the body. Examples of the former substance include agents which inhibit synthesis of genomic RNA or DNA of the virus, and agents which inhibit adsorption of the virus to the host cell. Examples of the latter substance include antiviral vaccines and immunostimulating substances. The meaning of the term "do not contain an antiviral active component" includes not only cases where the particles do not contain any antiviral active component at all, but also cases where the particles contain an antiviral active component at such a minute amount that the antiviral active component cannot exert its antiviral action against the target virus. In regard to the meaning of the above-mentioned "such a minute amount that the antiviral active component cannot exert its antiviral action", an amount of the active antiviral component contained in a unit volume of the particles is defined as concentration in particles. When the replication of the target virus cannot be inhibited by treating the virus with the active antiviral component in form of not being incorporated into particles at the same concentration as the above-defined concentration in particles, the concentration is considered to be "such a minute amount that the antiviral active component cannot exert its antiviral action". The polymer particles used in the present invention may be particles that do not contain any antiviral active component such as an antiviral drug at all.

The antiviral agent of the present invention may consist only of the polymer particles, or may be in a form of a dispersion liquid prepared by dispersing the particles in an appropriate solvent. For example, the antiviral agent of the present invention may be provided in a form of freeze-dried particles, or in a form of a particle dispersion containing the polymer particles at a concentration higher than the concentration at which the polymer particles are ordinary used, or at a ready-to-use concentration. In cases where the antiviral agent of the present invention is used as a pharmaceutical, one or more of known carriers such as vehicles and diluents may also be included to prepare a formulation suitable for the dosage form. The antiviral agent may contain only a single kind of polymer particles, or may contain two or more kinds of polymer particles (that is, a plurality of kinds of polymer particles containing different polymerization initiators/stabilizers).

When the antiviral agent of the present invention is incorporated into a sanitary article, the polymer particles adhere to virus particles before the virus enters into the body, so that the virus can be physically captured or infectivity of the virus particles can be eliminated. Thus, a sanitary article having excellent virus infection-preventing effect can be provided. Specific examples of the sanitary article include, but are not limited to, masks, white coats, protective clothing, gloves, goggles, contraceptive devices and agents, diapers, bed sheets, filters for air cleaners and air conditioners, room mists, hand soaps, gargles, sprays, and detergents. The sanitary article may be produced using a sanitary article material such as fibers, non-woven fabric or resin to which the polymer particles are attached or in which the polymer particles are kneaded, or may be produced by attaching the polymer particles to a sanitary article after its production. In cases of a liquid sanitary article, the polymer particles may be added or blended in any step during the production. For example, a mask comprising the antiviral agent of the present invention can exert an excellent effect on prevention of infection with viruses that occurs through droplet infection or airborne infection, such as infection with influenza virus, whose prevalence occurs every winter.

The antiviral agent of the present invention can be administered to a subject in need thereof for the purpose of treatment or prevention of virus infection. The "subject" herein is typically an animal, and includes animals such as mammals, birds, fishes, crustaceans, shellfishes/mollusks, reptiles, amphibians, and insects. In cases where the agent is administered to human, the dose is not limited. The polymer particles may be administered to adult human (with a body weight of about 60 kg) at a dose of usually about 0.001 g to 20 g, for example, about 0.1 g to 5 g, each time. In cases where the agent is used for another species of animal, the agent may be administered at a dose equivalent to the dose described above.

Examples of the administration method for the particles include parenteral administration such as inhalation, transmucosal administration, application, sprinkling on the skin, instillation, subcutaneous administration, intramuscular administration, intraperitoneal administration, intraarterial administration, intravenous administration, and rectal administration; and oral administration. More specifically, for example, the polymer particles may be suspended in physiological saline and parenterally administered by injection or the like. The polymer particles may also be orally administered as a capsule or a syrup. Besides systemic administration, topical application using a transdermal patch or an ointment is also possible. In cases where the polymer particles are administered to livestock, fowl, or farmed fish, the particles may be orally administered by addition to the feed. In cases where the polymer particles are used for disinfection of a medical instrument, agricultural/horticultural instrument or the like, the polymer particles may be dispersed in water, an alcohol solvent or the like in an amount of about 0.00001 g to 0.1 g, or at a concentration of about 0.0001 w/v % to 0.1 w/v %, and the instrument may be immersed in the resulting dispersion. In cases where the polymer particles are used for the purpose of controlling plant viral diseases, the amount of the particles applied to the plant is not limited, and may be appropriately selected depending on the degree of occurrence of the disease. The particle dispersion having the concentration described above may be sprayed on the plant body (including any parts of a plant individual, such as the root, stem, leaf, fruit, and flower), ground soil, pot soil, seedling box, and/or the like. Seeds may be disinfected by immersion of the seeds in a particle dispersion. By administering the polymer particles to a living body, or by bringing the polymer particles into contact with an instrument or the like, the particles can be brought into contact with the virus to be suppressed. By this, infectivity of the virus particles can be reduced or eliminated, and the replication of the virus in the living body and/or further transmission of the virus to other individuals can be prevented.

EXAMPLES

The present invention is described below more concretely by way of Examples. However, the present invention is not limited to the Examples below.

1. Production of Nanoparticles

According to the methods described in Patent Documents 8 and 9, nano-sized polymer particles containing an amino acid or a dextran were produced. More concretely, the procedure was as follows.

(1) Amino Acid Synthesis System

In 10 mL of 0.001 N HCl, 100 mg of amino acid was dissolved. The pH of the solution was adjusted to pH=3 as needed using 1 N hydrochloric acid. As the amino acid, glycine, alanine, or aspartic acid was used.

(2) Dextran Synthesis System

In 10 mL of 0.01 N HCl, 100 mg of dextran 60K was dissolved. The pH of the solution was adjusted to pH=2 as needed using 1 N hydrochloric acid.

To each of the solutions (1) and (2), 100 μL of nBCA was added with stirring, and the resulting mixture was stirred for 3 hours to perform polymerization reaction. The reaction solution was neutralized (pH 7.8) by adding 1 N NaOH dropwise thereto, and then stirred for additional 30 minutes. The reaction solution was subjected to centrifugal filtration using Centriprep (YM-10) filter (MILLIPORE) at 3500 rpm/15 minutes. To the liquid that has not passed through the filter, distilled water was added, and centrifugal filtration was carried out again to wash the polymerized particles. This centrifugal washing operation was carried out 4 times in total to obtain nano-sized polymer particles containing an amino acid or dextran.

Using a commercially available Zetasizer (manufactured by Malvern Inst., UK), the average particle diameter and the zeta potential were measured. The measurement results are shown in Table 1.

TABLE 1

| | Amino acid content (%) | Average particle diameter (nm) | Peak 1 (nm) | Peak width (nm) | Zeta potential (−mV) |
|---|---|---|---|---|---|
| Gly-Nano | 51.6 | 131 | 133 | 33.7 | 16.6 |
| Ala-Nano | 33.5 | 145.4 | 143 | 50.2 | 17.4 |
| Asp-Nano | 28.5 | 139.5 | 153.8 | 49.5 | 18.9 |
| D60-Nano | — | 148.5 | 163.7 | 56.3 | 11.7 |

2. Study of Antiviral Effect of Nanoparticles

As a sample virus, cyprinid herpes virus 3 (CyHV-3), which is a fish disease virus, was used. As sample nanoparticles, the four kinds of nanoparticles synthesized as described above were used.

(1) Confirmation of Toxicity to Carp Cells

Prior to the study of the antiviral effect, toxicity of the nanoparticles to carp cells was investigated as follows. Cells derived from a carp fin were cultured on 3.5-cm dishes to allow formation of a single cell layer. Nanoparticles at various concentrations (a 10-fold dilution series prepared from an undiluted liquid (1-fold dilution) at a particle concentration of 10 mg/mL) were added to the dishes. Changes in the cells were observed under the microscope to determine the presence or absence of toxicity. As a result, none of the four kinds of particles showed toxicity to the carp fin cells even at the concentration of as high as 10-fold dilution (1 mg/mL).

(2) Confirmation of Antiviral Effect of Nanoparticles

Using 0.2% CyHV-3 solution as an undiluted virus solution, a 10-fold dilution series was prepared and used in an antivirus test. The 10-fold dilution of each kind of nanoparticles was mixed with the virus solutions, and the resulting mixtures were incubated at 4° C. for 1 hour. Each mixture was then added to single-layer cultured cells ($10^6$ cells/well) derived from a carp fin. After incubation at 25° C. for 24 hours, DNA in the cells was extracted, and the copy number of a viral gene (ORF89 gene) was determined by real-time PCR.

<DNA Extraction>

Cells were peeled off from each well of a 24-well plate using a micropipette, and the collected cell suspension was transferred to 2-ml microtubes. After addition of 0.2 μL of Proteinase K, the cell suspensions were lightly vortexed, and incubated at 55° C. for 2 hours. Thereafter, 300 μL of phenol/chloroform was added to each suspension, and centrifugation was carried out at 20° C. at 15,000 rpm for 5 minutes, followed by collecting 200 μL of the supernatant using a micropipette. After repeating the same operation three times, 500 μL of 100% ethanol and 20 μL of 3 M sodium acetate were added to the obtained supernatant, and the resulting mixture was stored at −30° C. overnight. The stored sample was then centrifuged at 20° C. at 15,000 rpm for 1 hour, and the supernatant was discarded by decantation. To the obtained precipitate, 1,000 μL of 70% ethanol was added, and centrifugation was carried out at 20° C. at 15,000 rpm for 10 minutes. The supernatant was then discarded by decantation, and the DNA precipitate was dried. After adding 30 μL of Tris-EDTA buffer solution thereto, DNA was suspended to provide a DNA sample.

<Real-Time PCR>

The amount of DNA extracted was measured using Q5,000 (TOMY), and the DNA concentration was adjusted to about 200 ng/μL by dilution with distilled water. Screening was carried out as follows. Into a PCR tube, 1.0 μL of cDNA solution, 5 μL of TaqMan Gene Expression Master Mix (Applied Biosystems), 0.5 μL of probe (CTTCCTCT-GCTCGGCGAGCACG; SEQ ID NO:1), 0.9 μL each of primers KHV-86F (GACGCCGGAGACCTTGTG; SEQ ID NO:2) and KHV-163R (CGGGTTCTTATTTTTGTCCTT-GTT; SEQ ID NO:3), and 1.7 μL of purified water were added, and real-time PCR reaction was carried out using Step One Plus™ real-time PCR System (Applied Biosystems) to determine the virus concentration. The PCR reaction was carried out as follows. First, heat denaturation was carried out at 95° C. for 10 minutes. Subsequently, 40 cycles of reaction, each composed of heat denaturation at 95° C. for 30 seconds and annealing/extension reaction at 60° C. for 1 minute, were carried out. The screening was carried out in two replicates.

Figures 1, 2:
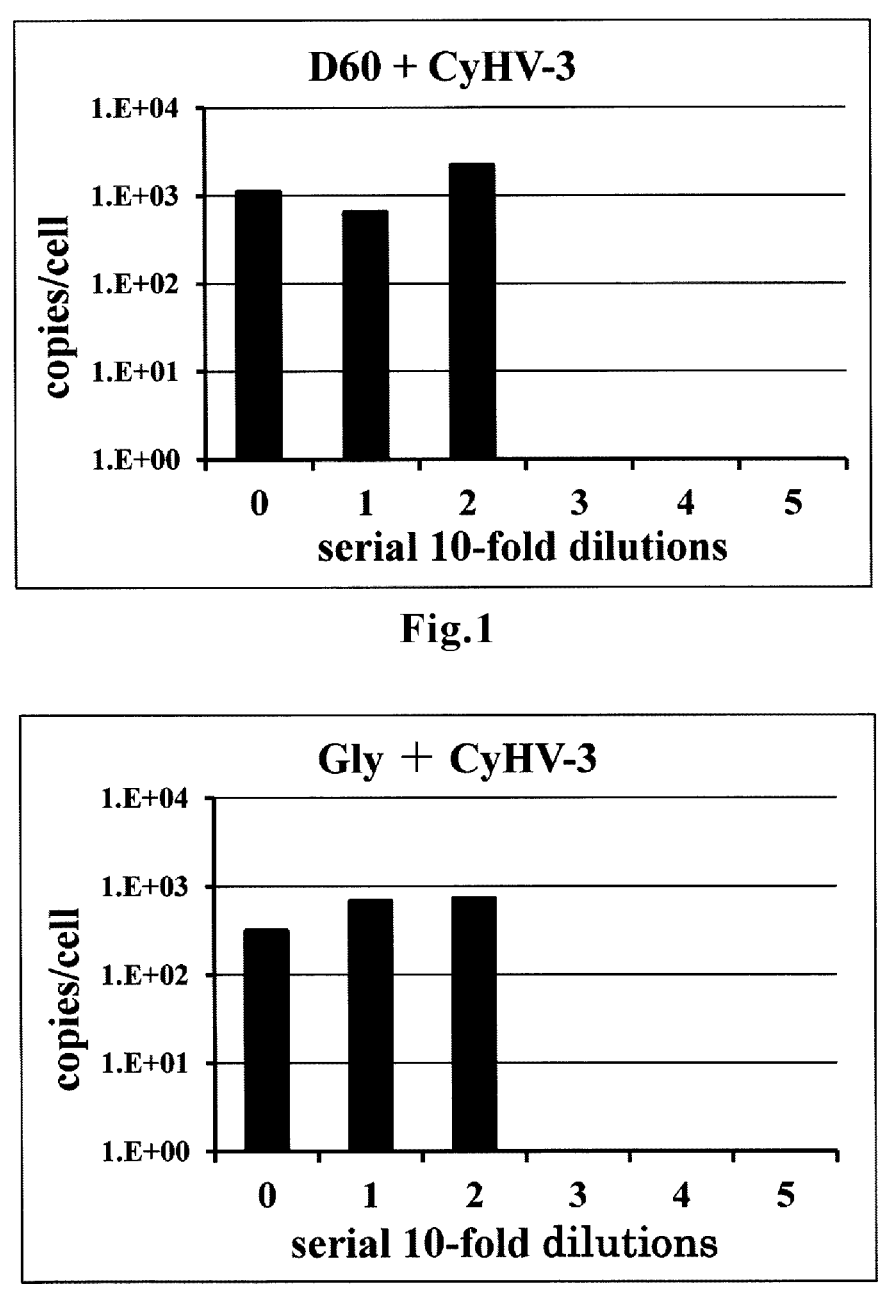
Figure 4:
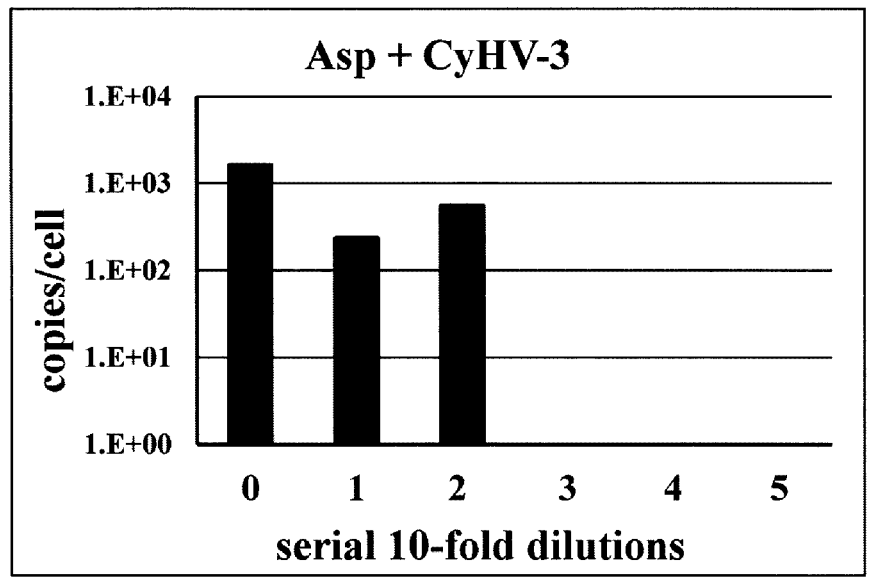
FIG. 4 shows results obtained by adding CyHV-3 treated with aspartic acid-containing nanoparticles to carp fin cultured cells, incubating the cells for a predetermined period, and then determining the copy number of the ORF89 gene in the cells.
Figure 5:
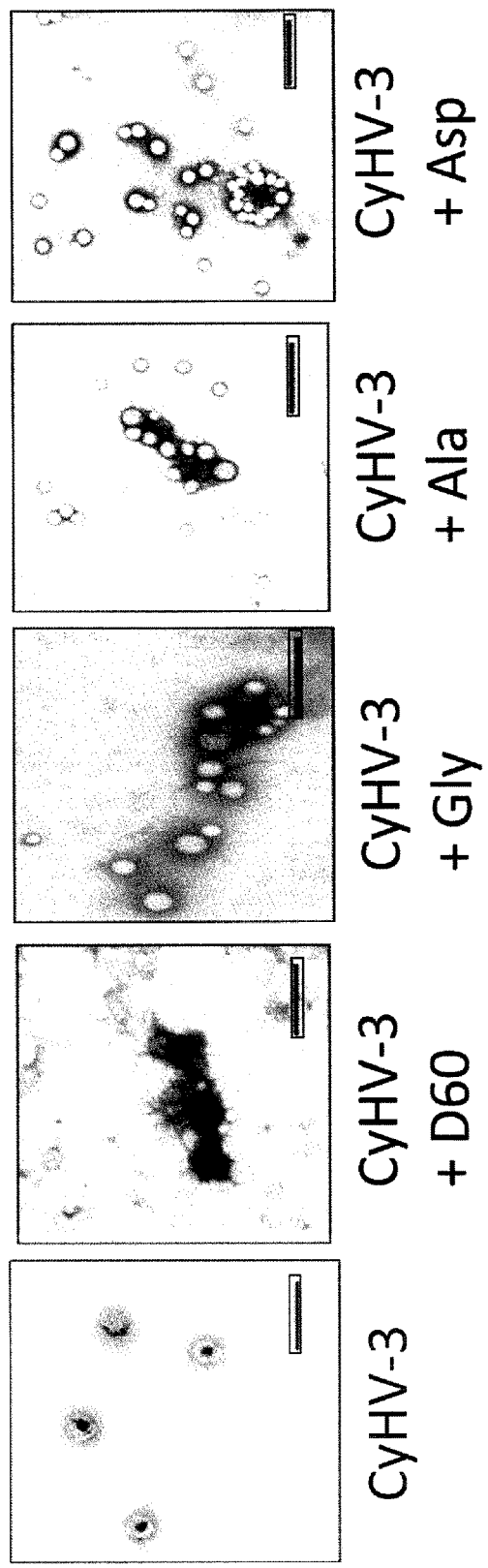
FIG. 5 shows transmission electron microscope images of the nanoparticle-treated CyHV-3. Scale bars represent 500 nm.

The results of determination of the gene copy number per cell are shown in FIG. 1 to FIG. 4. The abscissa represents the dilution ratio of the virus treated with the particles, and 0 corresponds to the undiluted solution (0.2% virus solution). The ordinate represents the gene copy number per cell. It could be confirmed that all four kinds of nanoparticles could completely suppress (to below the detection limit) the intracellular viral replication when the virus concentration is not more than $0.2 \times 10^{-3}\%$ ($10^3$-fold dilution).

3. Electron Microscopic Observation of Virus Particles Treated with Nanoparticles CyHV-3 (moi=1) was inoculated into carp fin-derived cells in 10 small flasks (25 cm$^2$), and the cells were then incubated at 25° C. for 10 days, followed by subjecting freezing at −80° C. and thawing twice. Subsequently, the suspension was transferred to a 50-ml centrifuge tube, and centrifugation was carried out at 5,000 rpm at 4° C. for 30 minutes, followed by collecting the supernatant. The supernatant was then subjected to ultracentrifugation (Beckman) at 40,000 rpm at 4° C. for 1.5 hours to precipitate the sample of interest. After discarding the supernatant, the pellet was resuspended in 500 μL of serum-free DMEM medium. The resulting suspension was carefully overlaid on layered 30%/40%/50% sucrose, followed by performing ultracentrifugation at 40,000 rpm at 4° C. for 1.5 hours. Thereafter, a band detected above the 50% layer was collected, and dialyzed against 500 mL of PBS overnight to provide a sample virus solution. With 50 μL of the sample virus solution, 5 μL of each of the four kinds of nanoparticle solutions was mixed. The reaction was allowed to proceed for 24 hours, and observation was then carried out using a transmission electron microscope H-7100 (Hitachi, Ltd.)

FIG. 5 shows the obtained electron microscopic images. Adhesion of nanoparticles to the virus envelope, causing destruction of the envelope and exposure of the capsid, could be observed.

The invention claimed is:

1. A method for reducing or eliminating infectivity of a virus(es), or for suppressing replication of a virus(es), in or on a sanitary article, said method comprising attaching particles having a particle diameter of not more than 5 μm to said sanitary article or incorporating said particles into said sanitary article, and bringing an effective amount of said particles having a particle diameter of not more than 5 μm into contact with said virus(es), wherein said particles are polymer particles whose repeat unit comprises a structure represented by the following General Formula (I):

(I)

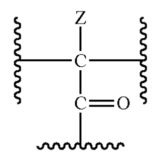

wherein Z represents an electron-withdrawing group.

2. The method according to claim 1, wherein in the General Formula (I), Z represents cyano, nitro, carbonyl, carboxy, or trifluoromethyl.

3. The method according to claim 2, wherein in the General Formula (I), Z represents cyano.

4. The method according to claim 1, wherein said structure represented by the General Formula (I) is a structure represented by the following General Formula (II):

(II)

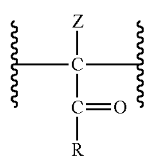

wherein Z has the same definition as in the General Formula (I); R represents hydrogen, hydroxy, $C_1$-$C_{10}$ alkyl, $C_1$-$C_{10}$ alkoxy, $C_6$-$C_{15}$ aryl, $C_6$-$C_{15}$ aryloxy, $C_7$-$C_{16}$ aralkyl, or $C_7$-$C_{16}$ aralkyloxy; and one or more carbon atoms constituting the carbon chain in R are optionally replaced by nitrogen, sulfur, and/or oxygen.

5. The method according to claim 4, wherein in the General Formula (II), R represents hydroxy or $C_1$-$C_{10}$ alkoxy.

6. The method according to claim 5, wherein in the General Formula (II), R represents n-butoxy.

7. The method according to claim 1, wherein said polymer particles are particles produced by polymerizing at least one monomer represented by the following General Formula (III):

(III)

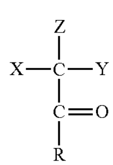

wherein Z has the same definition as in the General Formula (I); R represents hydrogen, hydroxy, $C_1$-$C_{10}$ alkyl, $C_1$-$C_{10}$ alkoxy, $C_6$-$C_{15}$ aryl, $C_6$-$C_{15}$ aryloxy, $C_7$-$C_{16}$ aralkyl, or $C_7$-$C_{16}$ aralkyloxy; and one or more carbon atoms constituting the carbon chain in R are optionally replaced by nitrogen, sulfur, and/or oxygen; and X and Y each independently represents a group having a terminal carbon-carbon double bond, or X and Y together represent methylidene in the presence of at least one member selected from the group consisting of amino acids, amino acid derivatives, oligomers of amino acids, oligomers of amino acid derivatives, polymers of amino acids, polymers of amino acid derivatives, saccharides, and polysorbates.

8. The method according to claim 7, wherein in the General Formula (III), X and Y together represent methylidene.

9. The method according to claim 8, wherein said at least one monomer represented by the General Formula (III) comprises n-butyl-2-cyanoacrylate.

10. The method according to claim 7, wherein said particles are particles produced by polymerizing said at least one monomer in the presence of at least one member selected from the group consisting of amino acids, amino acid derivatives, oligomers of amino acids, oligomers of amino acid derivatives, and saccharides.

11. The method according to claim 10, wherein said particles are particles produced by polymerizing said at least one monomer in the presence of at least one selected from the group consisting of amino acids and saccharides.

12. The method according to claim 7, wherein said amino acid derivatives are at least one selected from the group consisting of creatine, ornithine, thyroxine, desmosine, hydroxyproline, hydroxylysine, phosphoserine, theanine, kainic acid, tricholomic acid, and sarcosine.

13. The method according to claim 7, wherein said amino acids are at least one selected from the group consisting of arginine, histidine, lysine, aspartic acid, glutamic acid, alanine, glycine, leucine, valine, isoleucine, serine, threonine, phenylalanine, tryptophan, tyrosine, cystine or cysteine, glutamine, asparagine, proline, methionine, β-alanine, γ-aminobutyric acid, carnitine, γ-aminolevulinic acid, and γ-aminovaleric acid.

14. The method according to claim 7, wherein said saccharides are at least one selected from the group consisting of monosaccharides having a hydroxyl group(s), disaccharides having a hydroxyl group(s), and polysaccharides having a hydroxyl group(s).

15. The method according to claim 11, wherein said particles are particles produced by polymerizing said at least one monomer in the presence of at least one selected from the group consisting of glycine, alanine, aspartic acid, and dextran.

16. The method according to claim 1, wherein the average particle diameter of said particles is less than 1000 nm.

17. The method according to claim 1, wherein said virus(es) is/are a virus(es) having an envelope.

18. The method according to claim 17, wherein said virus is at least one selected from influenza virus and herpes virus.

19. The method according to claim 1, wherein said sanitary article is a mask.

* * * * *